United States Patent
Soderholm

(10) Patent No.: US 10,285,629 B1
(45) Date of Patent: May 14, 2019

(54) PHYSICAL MOTION MONITORING AND COMMUNICATION SYSTEM

(71) Applicant: SOUND IMAGING, INC., San Diego, CA (US)

(72) Inventor: Steven Soderholm, San Diego, CA (US)

(73) Assignee: SOUND IMAGING, INC., San Diego, CA (US)

( * ) Notice: Subject to any disclaimer, the term of this patent is extended or adjusted under 35 U.S.C. 154(b) by 558 days.

(21) Appl. No.: 14/829,991

(22) Filed: Aug. 19, 2015

Related U.S. Application Data

(60) Provisional application No. 62/039,215, filed on Aug. 19, 2014.

(51) Int. Cl.
*A61B 5/11* (2006.01)
*A61B 5/00* (2006.01)
*A61B 5/055* (2006.01)
*G01R 33/28* (2006.01)
*G01R 33/567* (2006.01)
*H04N 7/18* (2006.01)
*H04N 7/10* (2006.01)
*H04N 5/232* (2006.01)
*G06K 9/00* (2006.01)

(52) U.S. Cl.
CPC .......... *A61B 5/1128* (2013.01); *A61B 5/0077* (2013.01); *A61B 5/055* (2013.01); *A61B 5/746* (2013.01); *G01R 33/283* (2013.01); *G01R 33/567* (2013.01); *G06K 9/00335* (2013.01); *H04N 5/23206* (2013.01); *H04N 7/102* (2013.01); *H04N 7/181* (2013.01); *H04N 7/188* (2013.01)

(58) Field of Classification Search
CPC ........... G06K 9/00335; H04N 5/23206; H04N 7/102; H04N 7/181; H04N 7/188
See application file for complete search history.

(56) References Cited

U.S. PATENT DOCUMENTS

| | | | |
|---|---|---|---|
| 6,422,748 B1 * | 7/2002 | Shepherd | A61N 5/103 250/505.1 |
| 2002/0060737 A1 * | 5/2002 | Hsieh | G08B 13/19602 348/207.99 |
| 2003/0153826 A1 * | 8/2003 | Jack | A61B 5/055 600/410 |
| 2006/0171453 A1 * | 8/2006 | Rohlfing | G08B 13/19632 375/240.01 |
| 2014/0275970 A1 * | 9/2014 | Brown | G01R 33/3692 600/413 |
| 2014/0378816 A1 * | 12/2014 | Oh | G01R 33/283 600/409 |

* cited by examiner

*Primary Examiner* — Gregory H Curran

(57) ABSTRACT

A motion monitoring system for healthcare surveillance with visual and audio alerts is provided to monitor patients and actively mitigate the damages due to patient movement. The system documents each event involving patient movement and the surrounding area in various medical setting. The system also has the ability for a specific monitoring of a single location and upon a motion detected, the system outputs an alert signal to trigger external devices, including but not limited to lights and sirens, to notify the healthcare device operator.

5 Claims, 10 Drawing Sheets component diagram of an exemplary motion detection system for motion detection within an MRI environment Figure 1 exemplary block diagram of a motion detection system Figure 2 a sample room setup with an imaging equipment and three cameras Figure 3 A cross section of the imaging equipment/camera setup in the patient area Figure 4 Exemplary logic processes for motion detection.

Figure 5 Perspective view of a control room setup

Figure 6 An exemplary setup coupled to a door security circuit

Figure 7 an exemplary screen view options available to a system user

Figure 8 component diagram of an exemplary motion detection system for motion detection within an MRI environment Figure 9 Block diagram of a camera used within an MRI environment

CIRCUIT SCHEMATIC DIAGRAM OF A CAMERA USED WITHIN AN MRI ENVIRONMENT

PHYSICAL MOTION MONITORING AND COMMUNICATION SYSTEM

PRIORITY

This application claims priority to U.S. provisional patent application 62/039,215, filed on Aug. 19, 2014, which is hereby incorporated by reference in its entirety.

BACKGROUND

Technical Field

The present invention relates generally to field of motion detection and recognition. More specifically, the present invention relates to physical movement detection and monitoring in the field of healthcare.

Background of the Invention

In healthcare, there are times when a patient is left alone during a test, such as a CT scan (X-ray computed tomography), magnetic resonance imaging (MRI), Positron emission tomography (PET), Single-photon emission computed tomography (SPECT), Radiation therapy, etc. During the test, it is desirable to observe the patient for the full duration of the test to make sure that the patient remains still.

In hospital rooms or other areas where a patient is left for long periods of time without direct healthcare staff contact, it is a challenge to keep the staff informed for patient moving in real-time.

During imagining scanning process, if the patient moves the results can be detrimentally affected, which may cause undesired issues, such as unacceptable scanning image, longer scanning time, or even patient safety due to longer exposure to scanning environment and additional exposure to radionucleiotides, x ray radiation and or contrast agents. Conventional tracking and recording of movement devices such as motion detection cameras, are typically either unable to monitor patient movement adequately or focus only on a target area without the function to interact with the equipment to pause scanning or alert the patient/user. In a diagnostic imaging setting, it is difficult to use these traditional cameras because the Electromotive force (EMF) emitted by the image scanning equipment during use could potentially cause interference and prevent these traditional cameras to function as they were intended. Also, the large magnetic field environment and/or ionizing radiation from CT are detrimental to camera's operation. More importantly, the EMF emitted by the cameras can affect the scanning equipment and cause artifacts in the scan images.

It would be desirable to have a patient motion detection system capable of operating within various healthcare diagnostic environments.

SUMMARY OF THE INVENTION

Embodiments of the invention relate to a system for physical movement detection and monitoring in the field of healthcare and method for its implementation.

In various embodiments, a motion monitoring system for healthcare surveillance with visual and audio alerts, optional modality equipment control/interaction, is provided to monitor patients and actively mitigate the damages due to patient movement. The system documents each event involving patient movement and the surrounding area in various medical setting. The system also has the ability to be used for a specific monitoring of a single location and upon a motion detected, the system outputs an alert signal to trigger external devices, including but not limited to lights and sirens, to notify healthcare device operator.

In some embodiments, the present invention allows the observing of patients with the ability to focus on the area of concerned movement. The system may operate using standard hardware along with a computer platform (or a server) to operate. The server receives informational inputs from digital or analog cameras, user interface, and a door circuit. The server analyzes each received frame for differences of contrast and blurred edges to detect movement. Detected movements are marked through a multi-colored meter (such as a tri-colored meter) on a computer monitor. Moreover audible tones may also be heard and visual alerts may be presented on the user interface. If any detected movement goes beyond a threshold, the system sends a pulse to an attached circuit to trigger a pause in the healthcare diagnosis (such as MRI or CT scan), with an on screen and verbal notification that the test is paused due to excessive movement. In one embodiment, the threshold is user defined allowing the operator to decide how much movement is acceptable. In one embodiment, the threshold is predetermined.

In some embodiments, the procedure room is a potentially hazardous environment so the system may be operated in a security mode, wherein the computer platform is notified to start recording once a motion is detected in the room and continues recording for a predetermined or user-defined time after movement has stopped. In the case of a non-test environment, this can be used to monitor patients that may not be actively visited, and the recording can show what happened, if an incident occurred.

The system may work with various healthcare imaging systems such as MRI's, CT, PET, or SPECT, etc. In some embodiments, the system may use a safety switch built in to existing imaging device for motion detection response. When the patient moves within a target area, the invention sends a signal to activate the safety switch causing the imaging device to pause the imaging scanning or test, holding the position until a device operator resumes the test.

In some embodiment, the camera is disposed within a healthcare imaging environment, such as inside a magnetic resonance (MR) environment to output an image signal. The system also comprises a modulator inside the MR environment (also preferably within the same camera housing) and coupled to the camera to receive the image signal and generate a modulated image signal with a shifted image signal frequency. The modulated image signal is transferred out of the MR environment via a shielded coupling path. The shifted image signal frequency is chosen such that the image signal has a frequency with a distance from the MR device operating frequency to avoid interference.

In some embodiment, a multiplexer disposed outside of the MR environment and coupled to the shielded coupling path. The shielded coupling path functions both as a power path and a signal transfer path. The multiplexer outputs a power signal to the shielded coupling path and extracting image signals over the shielded coupling path for image recording and analysis.

In some embodiments, the system may record a session into a media storage, such as a USB drive, an optical disk or an internal flash drive, etc. The recorded session may be watermarked including desired information such as date/time, available patient name and record number. In some embodiments, the system may operate in a secondary mode, wherein the system sends notification through e-mail or text message that the imaging room is being accessed without turning the imaging device off. Under this circumstance, the system also records (and time-stamps) the accessed session for later review.

BRIEF DESCRIPTION OF THE DRAWINGS

Reference will be made to exemplary embodiments of the present invention that are illustrated in the accompanying figures. Those figures are intended to be illustrative, rather than limiting. Although the present invention is generally described in the context of those embodiments, it is not intended by so doing to limit the scope of the present invention to the particular features of the embodiments depicted and described.

One skilled in the art will recognize that various implementations and embodiments of the invention may be practiced in accordance with the specification. All of these implementations and embodiments are intended to be included within the scope of the invention.

DETAILED DESCRIPTION OF THE PREFERRED EMBODIMENTS

In the following description, for the purpose of explanation, specific details are set forth in order to provide an understanding of the present invention. The present invention may, however, be practiced without some or all of these details. The embodiments of the present invention described below may be incorporated into a number of different electrical components, circuits, devices, and systems. Structures and devices shown in diagrams are exemplary embodiments of the present invention and are not to be used as a pretext by which to obscure broad teachings of the present invention. Connections between components within the figures may be modified, re-formatted, or otherwise changed by intermediary components.

Various embodiments of the invention are for physical movement detection and monitoring in the field of healthcare and method for its implementation. The motion monitoring system for healthcare surveillance is provided to monitor patients and actively mitigate the damages due to patient movement. The system documents each event involving patient movement and the surrounding area in various medical setting. The system also has the ability to be used as security software for the specific monitoring of a single or multiple locations and with the use of a solid-state relay can be used to trigger external devices, including but not limited to lights and sirens.

The motion monitoring system incorporates a computer server receiving data from a digital or analog camera and analyzing the contrast position from one frame to the next. The higher the frame rate and the higher the resolution the more accurate the invention is. Using a user defined or predetermined threshold, the server calculates the difference between one frame and the next. Any identified movements are marked through a color coated bar. Once the threshold is exceeded, the server triggers a safety alarm on the associate diagnostic equipment causing the on-going diagnostic process (such as a MRI imaging or CT scanning) to pause. At this point the diagnostic process will not start again until reinitiated by a device user. The motion detection system may be valuable for motion awareness situations. For example, a patient is in a coma situation (not moving) and the healthcare giver needs to know when the patient starts to move and be notified in real-time. Small movements in the body could also state that the person is coming out of a coma and should be notified to healthcare give so that the person may receive proper and on-time treatment.

Figure 1:
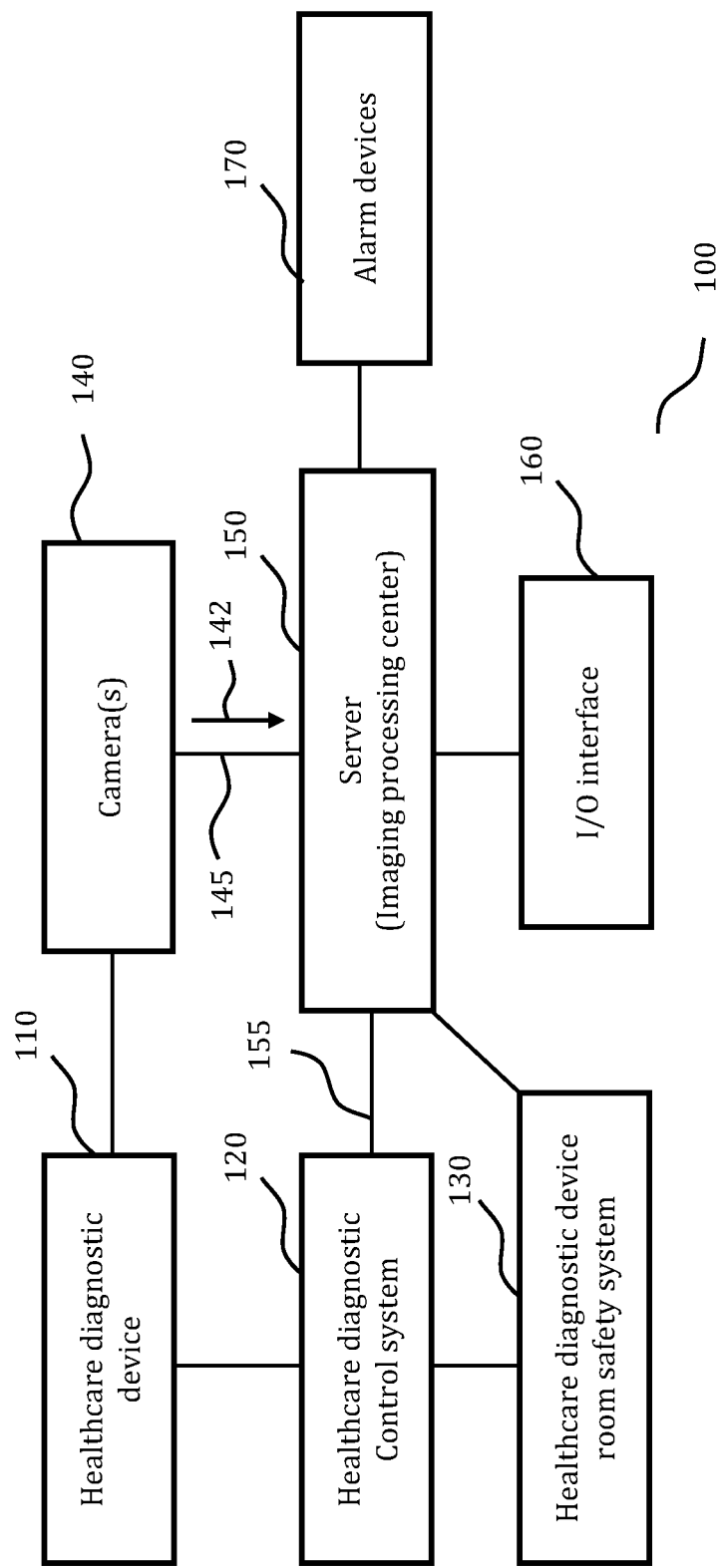
FIG. 1 shows an exemplary block diagram of a motion detection system with an embodiment of the present invention.

FIG. 1 shows an exemplary block diagram of a motion detection system with an embodiment of the present invention. The system 100 comprises at least one camera 140 for image capturing and image signal output image signal, a server (or computer platform) 150 for image signal receiving and movement analysis, a display for rendering processed information, and optionally alarm devices. The server 150 may be a workstation, a computer, a local server, or a cloud based server, etc. The server 150 comprises hardware, such as microprocessor, memory loaded with desired logic codes, media storage, internet communication interface, etc., to implement the aforementioned image receiving, analysis and output functions. In one embodiment, at least one camera 140 may couple to the healthcare diagnostic device 110 for image recording coordination. For example, the camera 140 starts taking images when the healthcare diagnostic device 110 starts operation. The healthcare diagnostic device 110 may be a MRI device, a CT scanner, PET scanner, SPECT scanner, linear accelerator, a medical ultrasound imaging device, etc. In another embodiment, the at least one camera 140 may be placed within an environment for motion detection only without coupling to any healthcare diagnostic device 110. The environment may be an ICU (Intensive Care Unit) room with a patient in a coma state.

The server 150 receives image signals 142 output from the at least one camera 140 via a coupling path 145 and analyzes the images for motion detection. The server 150 may couple to existing control system 120 of the healthcare diagnostic device 110 for device operation control. When a movement above a threshold is detected, the server outputs an alert signal 155 to the healthcare diagnostic device control system 120 to pause the device operation. The threshold may be a pre-determined threshold or a user-defined threshold stored within the server memory. The server may further output the alarm signal to an alarm device 170 to alert a device operator or user any movement above the threshold. The alarm device may be a siren, a flashing light, or a combination thereof. The server 150 couples to an I/O interface 160 accessible by the device user to show the image signal analysis results and receive user inputs. The I/O interface 160 may be a display, a touch screen, a printer, a keyboard, a mouse, a voice input device, or a combination thereof.

In some embodiment, the server 150 may couple to a healthcare diagnostic device room safety system 130 for further safety enhancements. Generally speaking, the healthcare diagnostic device room is a potentially dangerous environment when the diagnostic device is in operation. When the door is opened while the healthcare diagnostic device 110 is running a scan, this server sends a message to the healthcare diagnostic device 110 to pause the scan. In another embodiment, the camera automatically records images when the door of an ICU room is opened.

Figure 2:
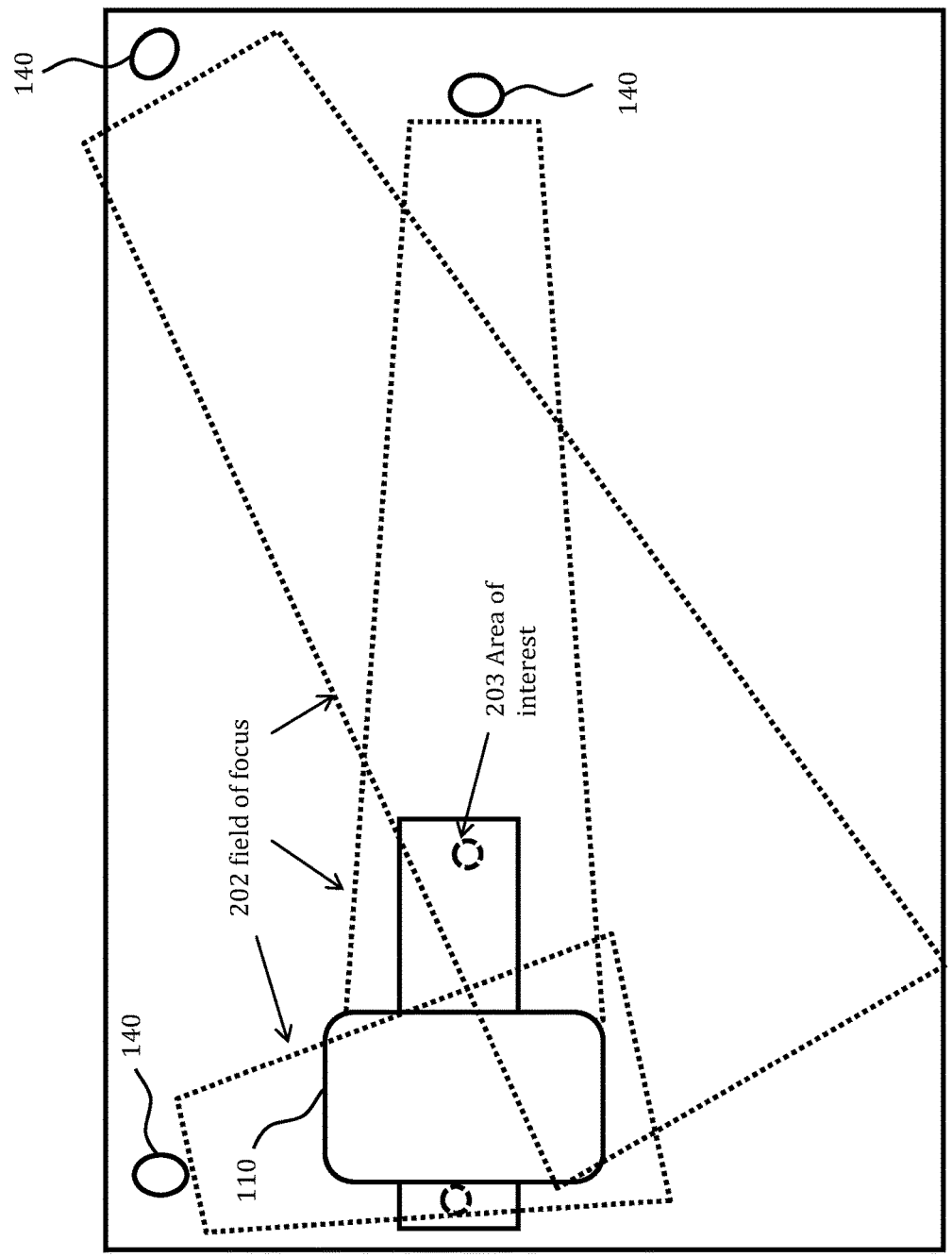
FIG. 2 shows a logic processes in accordance with an embodiment of the present invention.

FIG. 2 is a sample room setup with healthcare diagnostic device 110 and three cameras 140. The cameras may have focus areas that can be adjusted to anywhere in the field of vision from the camera. FIG. 2 is a top view showing the cameras 140, the field of focus 202 for the each cameras and the area of interest 203. Although there are three cameras shown in FIG. 2, it is understood that different numbers of camera may be used for motion detection depending on the room set-up and other parameters. In one embodiment, at least two of the cameras 140 have a crossed field of focus with the area of interest located within the crossed field of focus. Such arrangements would ensure that the area of interest is exposure to more than one camera for motion detection with desired accuracy.

In one embodiment, when the system is on a security mode, the cameras start recording as soon as the door is opened and continue recording while movement is detected. The server may send an email alert or trigger the alarm device 170 if the device 110 is not shut off within a predetermined time period, such as 90 seconds. In one embodiment, the system will have buffer storage holding a certain time period (such as 10 minutes) of recorded data and will be added to the patient session once monitoring starts. The system may also record additional certain time period (such as 10 minutes) after the testing finished.

Figure 3:
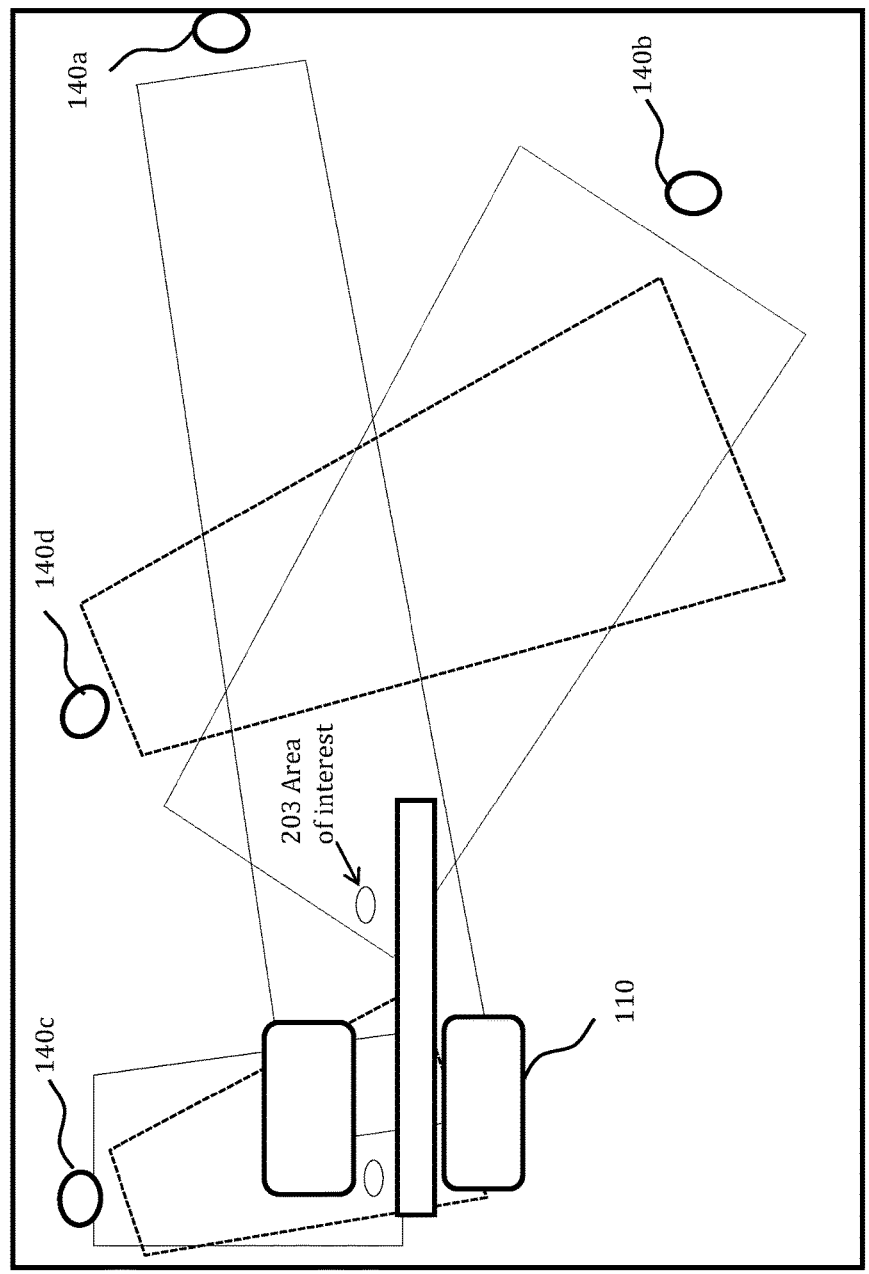
FIG. 3 is a sample room setup with three cameras with an embodiment of the present invention.

FIG. 3 shows a cross-section of the room layout showing the field of vision from the cameras and the area of focus where the software is watching for movement. As shown in FIG. 3, four cameras are used with camera 104a and camera 104b focused on the area of interest 203 (such as the patient), camera 104c focused on the area around the imaging device 110 and camera 140d focused to other area of the imaging device room.

Figure 4:
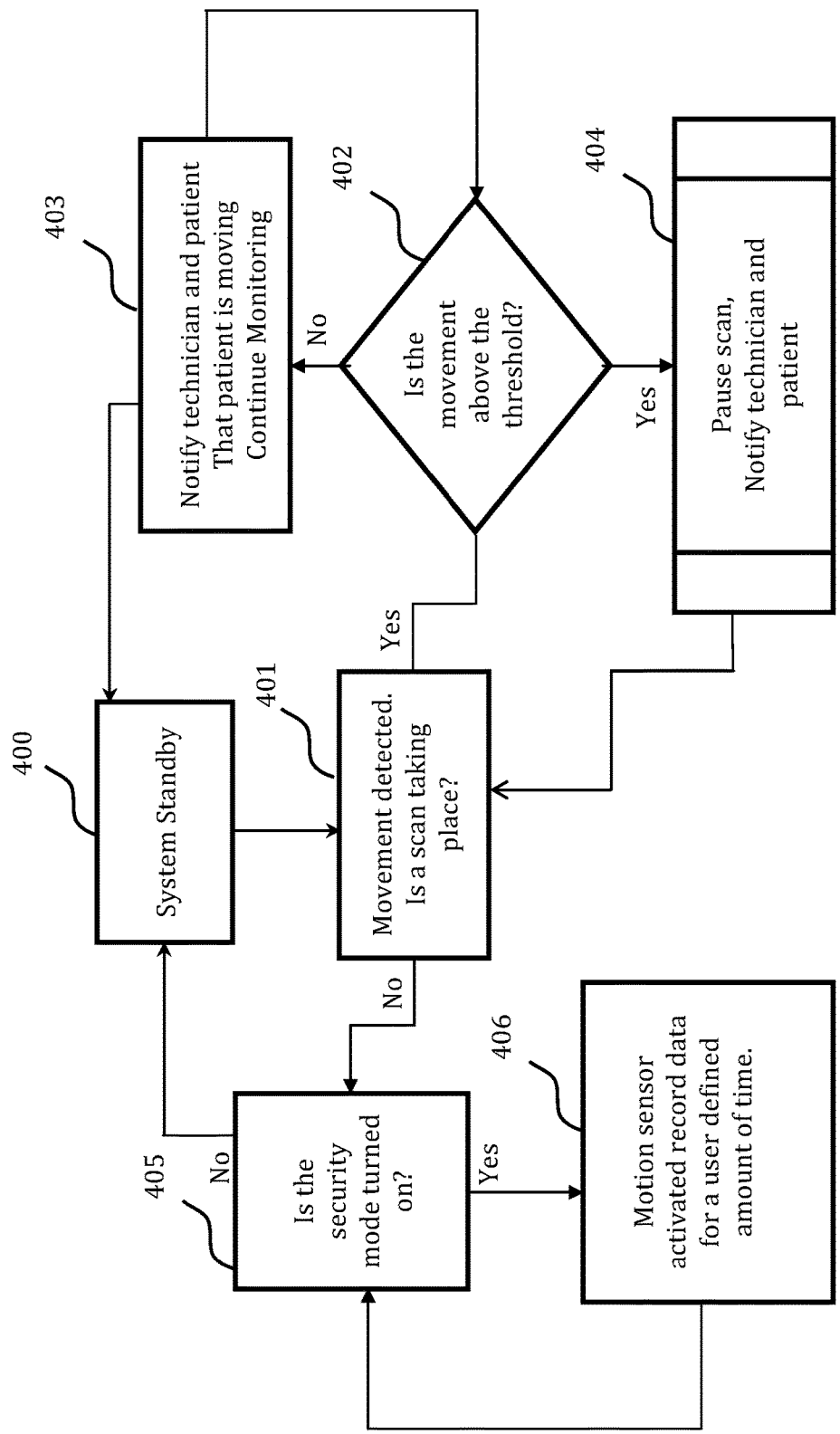
FIG. 4 gives a cross section of the imaging equipment/camera setup in the patient area.

FIG. 4 shows an exemplary logic processes in accordance with an embodiment of the present invention. At step 400, the system is in standby with the cameras 140 taking images and sending the images to the server 150 for analysis and motion detection. At step 401, the server checks whether the healthcare diagnostic device is taking a scan when a movement is detected. If yes, the process goes to step 402 to decide whether the detected movement is above a threshold. If no, the process goes to step 405, whether the server identify whether the system is running on a security mode. If the detected movement is identified to be below the threshold, the server 150 notifies a user (or a device technologist) that patient is moving in step 403. If the detected movement is identified to be above the threshold, the server 150 sends an alert message to the Healthcare diagnostic Control system 120 to pause the scan and/or informs the patient that the situation.

The threshold is predetermined or user-defined allowing the user to decide how much movement is acceptable. In one embodiment, if any one of the cameras detects a movement above the threshold, the server 150 sends the alert message to pause the scan. The thresholds for each of the cameras may or may not be the same, depending on at least one parameter selected from camera sensitivity, camera zoom level, camera location, etc. In some embodiments, the thresholds for each of the cameras may depend on the type of healthcare diagnostic process. For example, the motion threshold in MRI might be different than motion threshold in in PET. In another embodiment, the server 150 receives all imaging signals input from all of the cameras and makes an overall decision whether an excessive movement is detected for triggering the alarm message. For example, when two cameras are used to monitor one area of interest. If one camera detects a movement while the other camera does not detect a movement, the server may or may not output the alarm message to pause the scan. The overall decision algorithm may be preloaded within the server memory for the server to do the motion analysis and judgement.

When the server identifies that the system is running on a security mode, the process goes to step 406, wherein the server starts to record images for a user-defined amount of time. If the security system mode is not turned on, the process goes back to step 400 the cameras 140 taking images and sending the images to the server 150 for analysis and motion detection.

Figure 5:
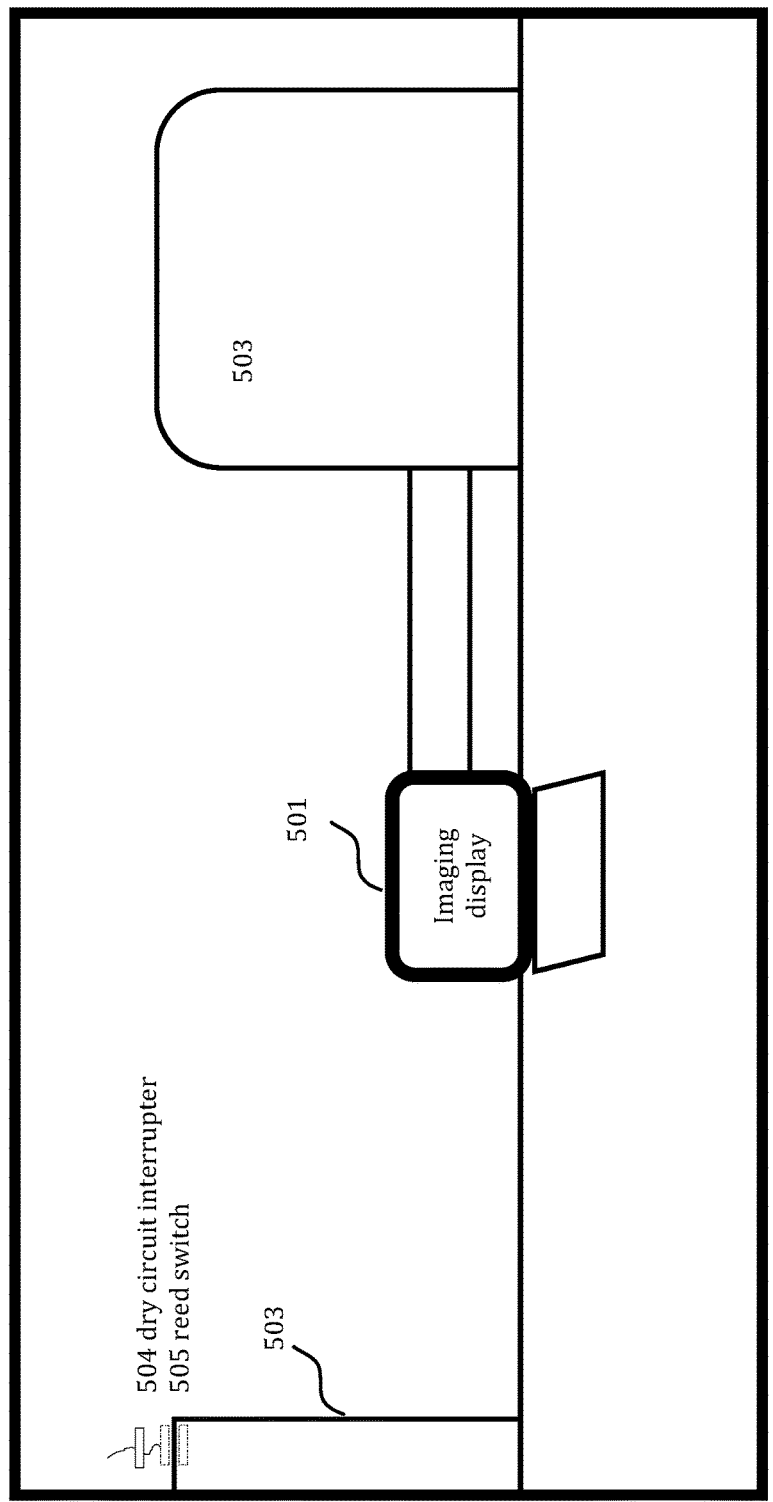
FIG. 5 shows an exemplary setup with an embodiment of the present invention.

FIG. 5 shows an exemplary setup of a control room with an embodiment of the present invention. Shown in FIG. 5 is a display 501, server 503, a dry circuit interrupter 504 attached in-line with the reed switch 505 which is installed on a door 503. The reed switch 505 is coupled to the server 503 for door opening/close information input.

Figure 6:
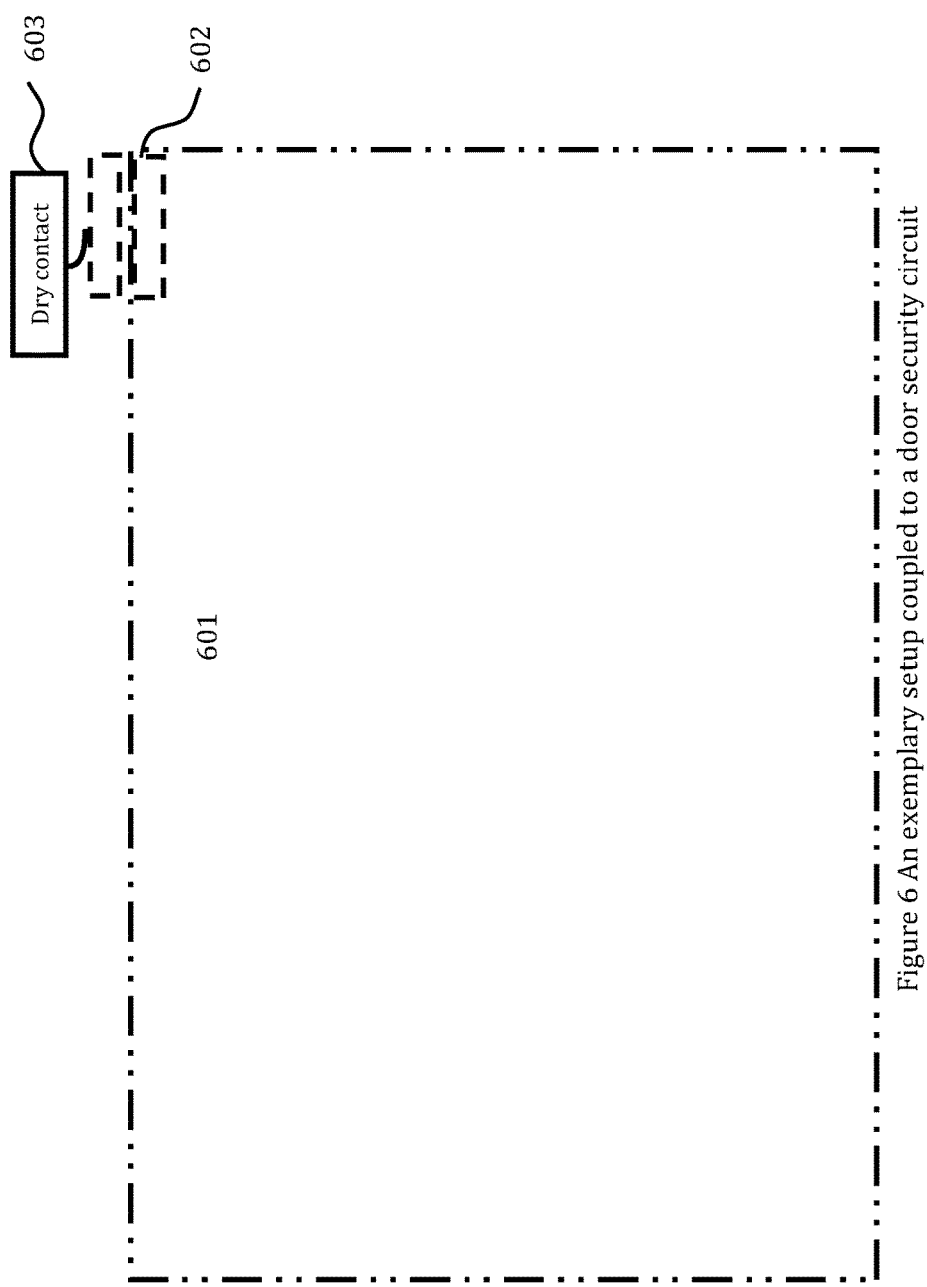
FIG. 6 shows an exemplary setup coupled to a door security circuit with an embodiment of the present invention.

FIG. 6 shows an exemplary setup coupled to a door security circuit with an embodiment of the present invention. A dry contract 603 and an interrupter 602 are installed on a door 601. When the door is open, the dry contract 603 triggers the interrupter 602 to pause the ongoing scanning process of the healthcare diagnostic device 110.

Figure 7:
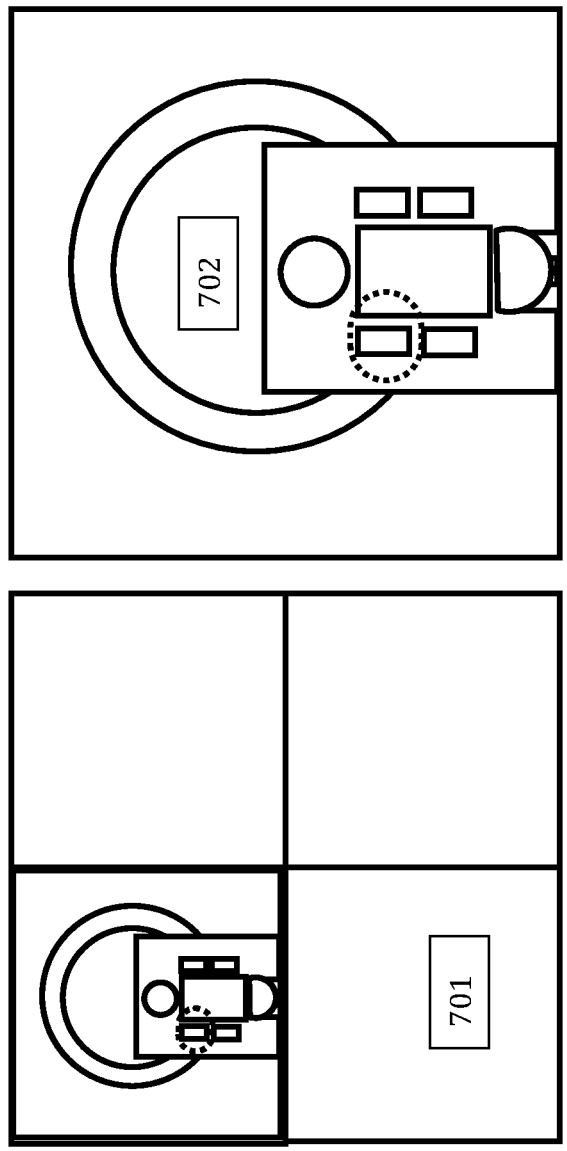
FIG. 7 shows an exemplary screen view options available to a system user.

FIG. 7 shows an exemplary screen view options available to a system user. Option 701 shows the four sub-screens corresponding to the perspective cameras. In one embodiment, the screen also shows additional watermarked information, such as patient name, date and time, etc. Option 702 shows a full screen for the focused view.

Figure 8:
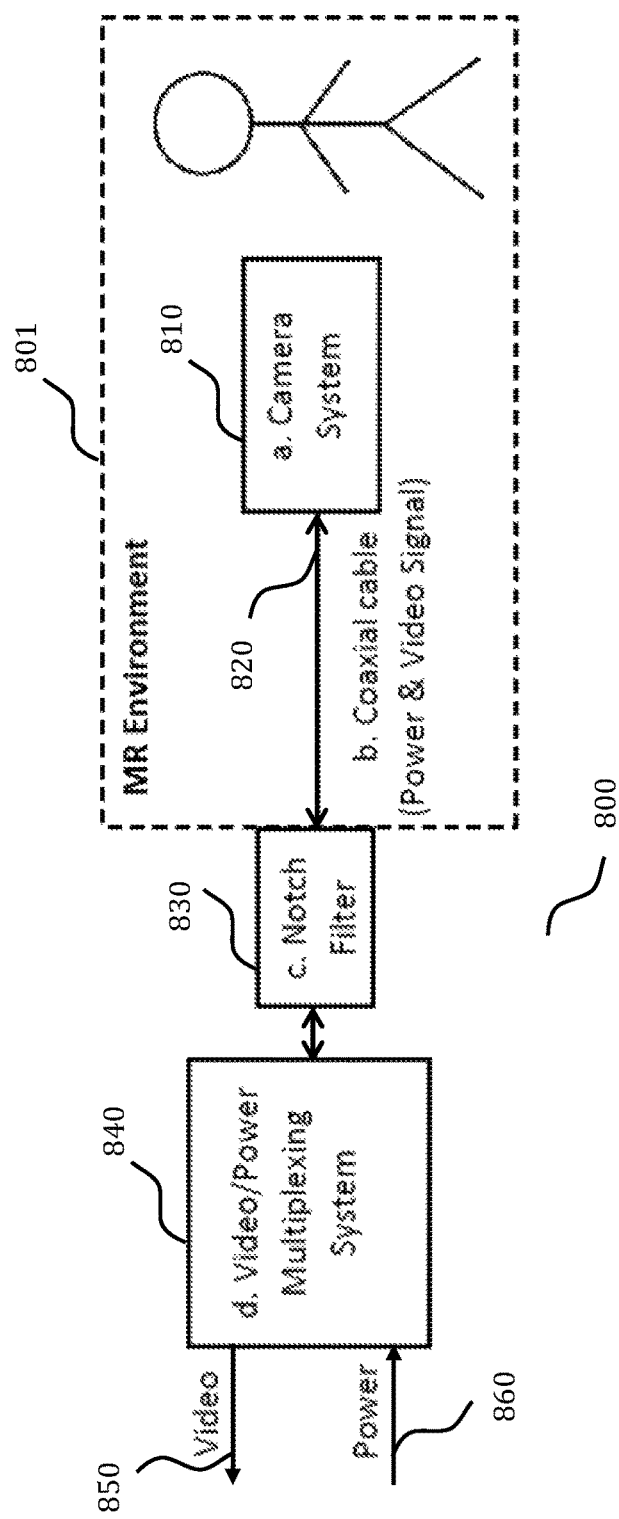
FIG. 8 shows a component diagram of an exemplary image generating system for motion detection within an MRI environment in accordance with an embodiment of the present invention.
Figure 9:
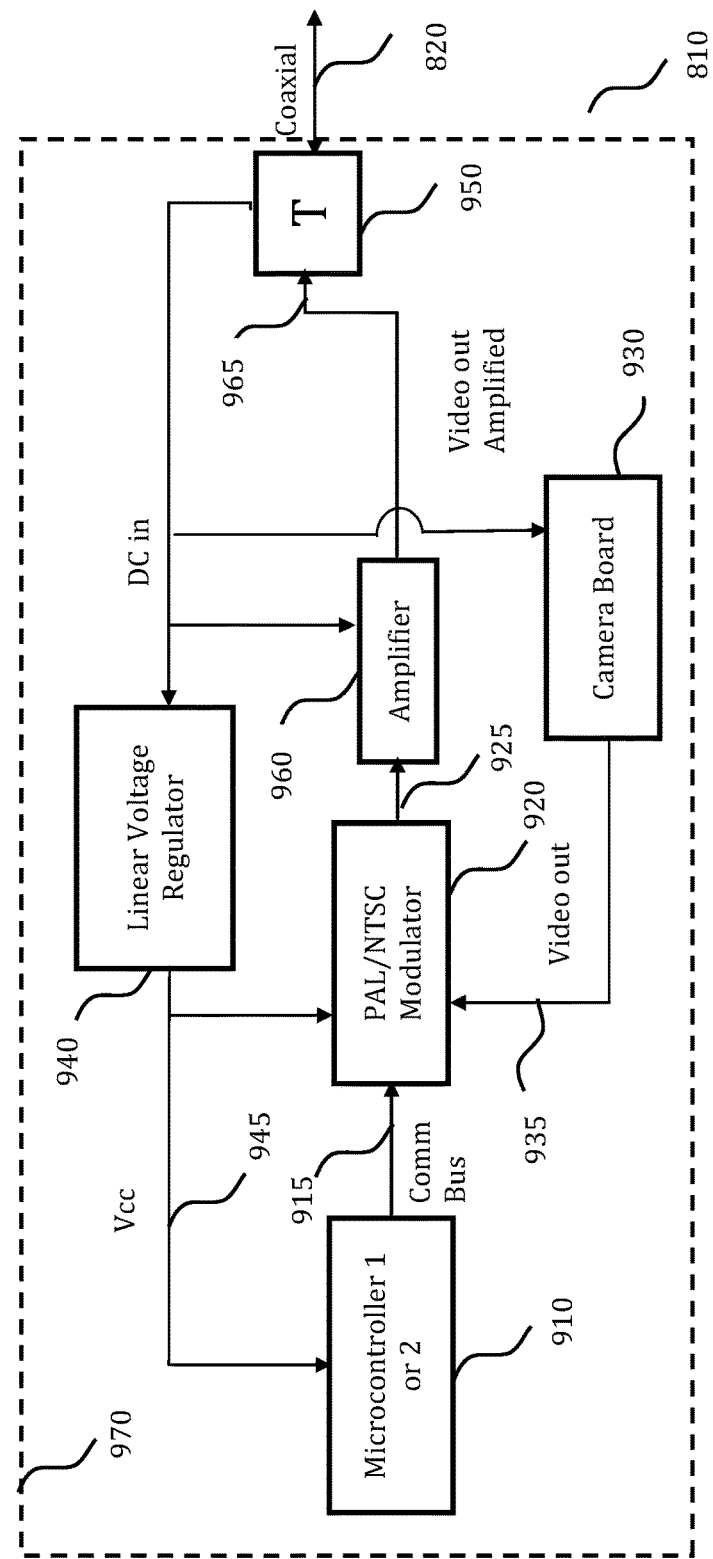
FIG. 9 shows a block diagram of a camera used within an MRI environment in accordance with an embodiment of the present invention.
Figure 10:
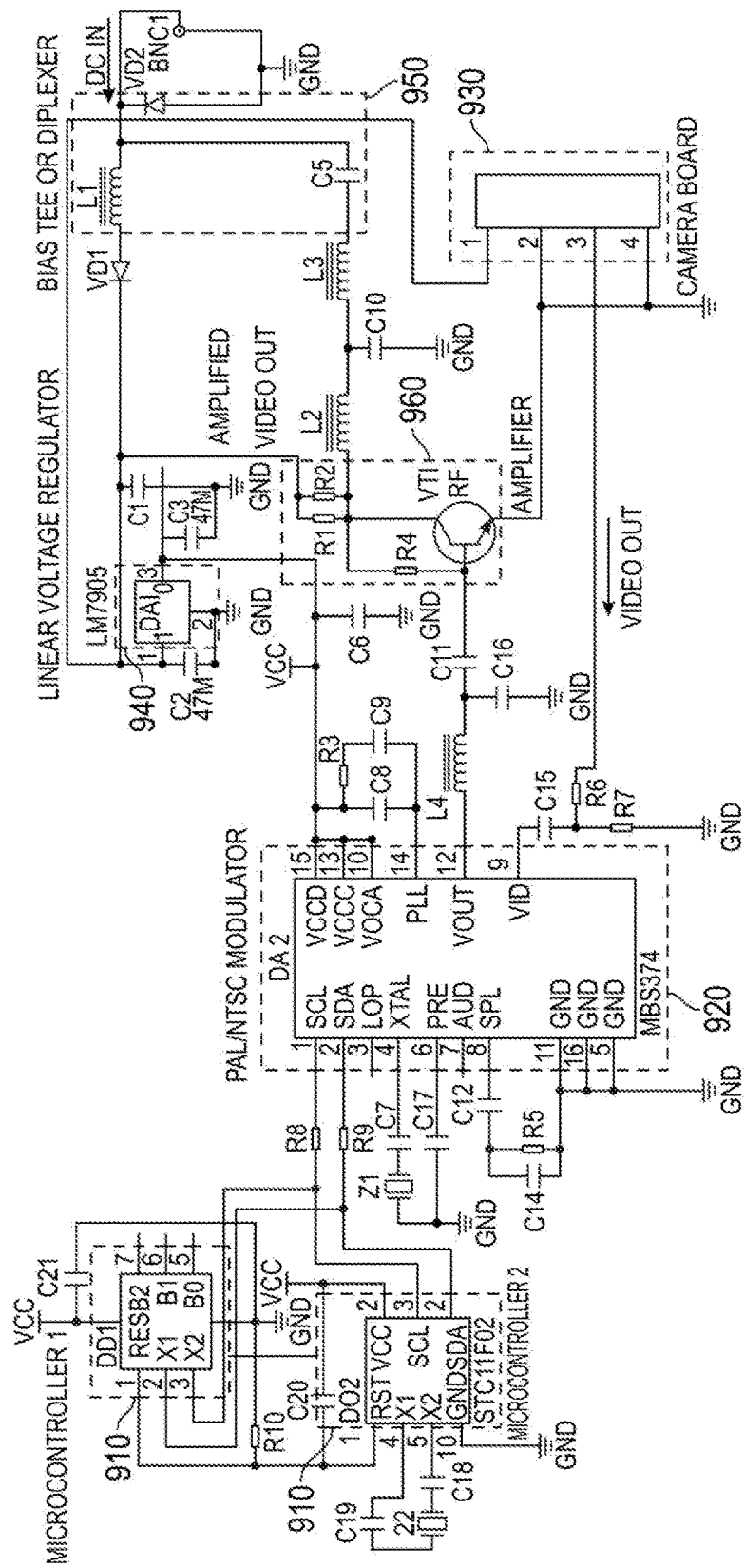
FIG. 10 shows a circuit schematic diagram of a camera used within an MRI environment in accordance with an embodiment of the present invention.

Applicable to MRI:

In a preferred embodiment, the present invention provides an MRI compatible patient motion monitoring system as shown in FIGS. 8-10. From the moment a person and/or ferrous metal enters the MRI scan room many things can happen due to the rooms unique properties. The present motion monitoring system records any detected motion event, and label/watermark the recording for future review and analysis.

Ferrous metal can also be introduced into the MRI scan room either by being tossed in alone or brought in with a person. The first situation could cause damage to the MRI scanner and having a video/audio record could help in find the perpetrator or instantly alerting the MRI scanner operator that this event has happened and record the event. The second situation, where a person carries a ferrous object in on their person, the person could be injured and/or stuck to the MRI scanner's magnet, both safety issues. Again, in a preferred embodiment, the present invention could instantly alert the MRI scanner operator to the situation and again, record the event. This could happen on nights and weekends when the MRI scanner operator is not onsite. In a preferred embodiment, the present invention will monitor the incident, record it, and remotely alert any individual assigned to the systems customizable remote alert options.

Due to the sensitive nature of the MRI scanning room, the operator cannot stay in the room next to the patient, so there is no capacity for bedside monitoring of the patient, but the present invention would allow the operator to monitor the patient from the control room. In a preferred embodiment of the present invention, the present invention will also allow communication between the patient and the operator.

Even when patient moves slightly, the image quality is reduced due to the movement. If the quality is compromised enough, the series (the sequence of scans in the healthcare diagnostic imaging process) may have to be redone. This will typically result in a loss of approximately ten minutes time. If the Series has to be redone, then the patient is inconvenienced by having to remain in the MRI scanner's bore, the patient may have additional contrast agent injected (cost and safety issue), and the MRI scanner operator has to duplicate work, in turn, other patients in the healthcare facility may be affected by the back-up. If the image quality is marginally bad due to the movement, the MRI scanner operator will have to decide whether to continue with the scan and not re-do the Series or to not continue and re-do the entire Series. If operator chooses to continue, then there is a chance that the unsatisfactory image quality Series could cause an improper medical diagnosis, which in turn is a safety issue.

The monitoring system monitors a patient's movement. In a preferred embodiment, even if there is a slight movement, the system announces over the MRI scanner's patient audio address system and to the MRI scanner operator's public address system, and allows the operator to request for the patient to hold still. If the movement is above a threshold, then the MRI Scanner is paused, a slightly different announcement will be made over both address systems, the scanner does not start again until the operator resumes the process.

Whether or not the MRI scanner's bore has an existing camera surveillance system, the present motion monitoring system allows the operator to do additional things beyond staring at the screen to monitor the patient. The motion monitoring system features MRI compatible digital or analog cameras, the dry circuit, and the hardware/software setup.

FIG. 8 shows a component diagram of an exemplary image generating system 800 for motion detection within an MRI environment in accordance with an embodiment of the present invention. The image generating system 800 comprises at least one camera 810 disposed inside an MR environment. The at least one camera 810 takes images and transfers those image signal out of the MR environment via a shielded coupling path 820 for image processing (motion detection and analysis, etc.). The camera 810 is a MR compatible camera capable of operation under MR environment.

In some embodiments, a filter 830 is disposed outside of the MR environment 801 and coupled to the shielded coupling path 820 to remove noise from the MR environment. The filter may be a notch filter with a band-stop center frequency tuned to an operating frequency of the MR environment. For example, the filter's center frequency is tuned to the operating frequency of the MRI which is 64 MHz for a 1.5 T machine and 128 MHz for a 3 T machine.

In some embodiments, the system further comprises a multiplexer 840 disposed outside of the MR environment and coupled to the shielded coupling path. The multiplexer outputs a power signal 860 to the shielded coupling path and extracts image signals 850 over the shielded coupling path. The extracted image signals 850 are sent to the server 150 for image recording, motion detection and analysis. The shielded coupling path is a shielded coaxial cable, or preferably a quad shielded coaxial cable for minimized EM interference.

FIG. 9 shows a block diagram of a camera used within an MRI environment in accordance with an embodiment of the present invention. The camera 810 comprises a microcontroller, a modulator 920, a camera board 930, a voltage regulator 940, a diplexing circuit 950, and a non-magnetic housing 970 for component packaging. Preferably, the housing is an aluminum or a copper alloy housing. The aluminum or a copper alloy housing may act as a faraday cage to prevent RF interference.

The camera circuit 930 outputs an image signal (or a video signal comprising a plurality frames of images) 935 to the modulator 920 for the generation of a modulated image signal 925 with a shifted image signal frequency (such as 300 MHz). A microcontroller 910 couples to the modulator and provides a signal 915 with a desired tuning frequency to the modulator for the modulation of the image signal output from the camera circuit 930. The voltage regulator 940 couples to the shielded coupling path and output a regulated voltage 945 to power at least one of the modulator 920, the microcontroller 910, the amplifier 960 and the camera circuit 930. Preferably, the voltage regulator 940 is a linear voltage regulator without any switching electronics to avoid any further switching noises.

In some embodiment, the modulated image signal 925 is sent to an amplifier 960 for the generation of an amplified image signal 965 before outputting via the coaxial cable 820. The diplexing circuit 950 is disposed within the non-magnetic housing 970 and functions as an interface of the camera to couple to the coaxial cable 820 directly. On one hand, the voltage regulator 940, the camera board 930 and the amplifier 960 receive power from the diplexing circuit 950. On the other hand, the amplifier outputs the amplified image signal 965 to the coaxial cable 820 through the diplexing circuit 950.

In an alternative embodiment, the camera board 930 and the amplifier 960 may also be configured to receive power from the voltage regulator instead of the diplexing circuit 950 directly.

FIG. 10 shows a circuit schematic diagram of a camera used within an MRI environment in accordance with an embodiment of the present invention. As shown in FIG. 10, the diplexing circuit 950 is an L-C based circuit. Power signal is extracted via a coupling inductor and a diode allowing unidirectional current flow. The amplified image signal 965 is coupled via a serial capacitor path. In some embodiments, all the capacitors used for circuits within the MRI environment are non-magnetic capacitors.

Shown in FIG. 10 are actually 2 microcontrollers 910 coupled to the modulator 920. These 2 microcontrollers may have the same or different shifting frequencies. In operation, there is only one microcontroller being functioned to provide the signal 915 with the desired tuning frequency. Alternatively, the camera 810 may only comprise one microcontroller for simplified hardware structure.

Applicable to Computerized Axial Tomography (CT):

Due to the hazardous nature of prolonged exposure to X-Rays, it is not advisable for the technologist to be in the patient area during the test; while the test is being performed it is important that the patient does not move. Doing so can cause an inconclusive test due to distortions (artifacts) in the CT scan image which may not be picked up during the scan.

Causing a loss of time and doubling the exposure of radiation to the patient. Also, the patient may then need an additional contrast agent injection, increasing costs and patient safety. The invention requires digital or analog cameras and the dry circuit, along with the software/hardware setup.

Applicable to Nuclear Medicine (PET and SPECT):

Due to the fact that patients are subject (through swallowing, injection or inhalation) to radioactive tracers they are exposed to ionizing radiation. The metabolism of said radioactive tracers also make the test time sensitive. While the test is being performed it is important that the patient does not move, a distracted technologist may miss that a patient is moving enough to cause a blurred test image. A blurred image can potentially cause inconclusive test results, requiring the patient to retake the test leading to further exposure to ionizing radiation. This invention will notify the technologist of the issues with the patient moving. The secondary application of the invention will also monitor the equipment for anyone being in the area which may allow anyone not meant to be identified. The invention requires digital or analog cameras and the dry circuit, along with the software/hardware setup.

Applicable to Radiation Therapy:

During radiation therapy, regions of the patient's body that contain tumor cells are exposed to a concentrated ionizing radiation beam through linear accelerators. If the patient moves during the procedure healthy tissue will be exposed to the beam compromising patient health. Therefore it is imperative that the procedure is paused or stopped if the patient is moving. This invention will notify radiologic technologist and automatically stop the procedure if sufficient patient motion is detected ensuring patient safety. The secondary application of the invention will also monitor the equipment for anyone being in the area which may allow anyone not meant to be identified. The invention requires digital or analog cameras and the dry circuit, along with the software/hardware setup.

Applicable to Patient Safety:

During a medical imaging or procedure, a patient can fall off the patient stretcher or diagnostic table. This is a safety issue for the patient and a potential legal issue for the facility. The invention will have the ability to record the event, watermark the event, be searchable and be produced at a later time for review.

Applicable to Intensive Care Unit (ICU):

The targeted area can be set to a very low threshold and be used to monitor patients that are in vegetative states, comas, or paralyzed. This system will allow staff to be notified of a change in patient status faster than rounds will. The advantages of the present invention include, without limitation, increased productivity of the workload during patient studies as well as freeing-up healthcare personnel. By implementing the present invention, a single operator can, for example, both perform the study and monitor the patient to allow the completion of the study. If the present invention detects motion the operator can communicate with patient to ensure the patient is comfortable and able to continue the study. The present invention allows for the observing of patients in any condition with the ability to focus on the area of concerned movement.

The present invention can be used for observing patients in any medical setting. It also has the ability to be used as security software for the specific observing of a single or multiple locations and with the use of the solid-state relay can be used to trigger external devices, including but not limited to lights and sirens.

The present invention might also incorporate the custom-built software to perform some additional tasks, such as tracking movement of a targeted individual or alerting an operator of light and/or extreme motion of targeted individual via visual and audio alerts. Further, the present invention may be used in conjunction with an interactive touchscreen computer to interact with the custom software. Further, the present invention might be able to send signals to interact with a healthcare facility's other devices.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

While various embodiments have been described above, it should be understood that they have been presented by way of example only, not limitation, and various changes in form and details may be made. Where methods described above indicate certain events occurring in certain order, the ordering of certain events may be modified. Additionally, certain of the events may be performed concurrently in a parallel process when possible or performed sequentially. Any portion of the apparatus and/or methods described herein may be combined in any combination, except mutually exclusive combinations. The embodiments described herein can include various combinations and/or sub-combinations of the functions, components and/or features of the different embodiments described.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the invention.

The invention claimed is:

1. A movement detection and monitoring system located inside a magnetic resonance environment, the system comprising:
   a) at least one camera to capture images and output an image signal comprising a plurality of frame images, wherein the camera has a camera circuit coupled to 1) a modulator to receive the image signal and generate a modulated image signal with a shifted image signal frequency, wherein the camera circuit and modulator are housed within a non-magnetic housing and 2) a shielded coupling path, which is also coupled to the modulator, wherein the shielded coupling path is a quad shielded coaxial cable that provides a power signal to the camera circuit and modulator from outside the magnetic resonance environment and transfers the modulated image signal out of the magnetic resonance environment,
   b) a server coupled to the at least one camera to receive the image signal and coupled to a healthcare diagnostic device, the server performing movement detection, wherein if a detected movement is above a threshold, the server outputs an alert message to a healthcare diagnostic device notifying the technician and patient and triggering a pause to the scanning process, or
   wherein if a detected movement is below a threshold, the server outputs an alert message to a healthcare diagnostic device notifying the technician and patient and the scanning process continues.

2. The movement detection and monitoring system of claim 1 wherein the server starts recording the captured images once a movement is detected and continues recording for a predetermined time after the movement has stopped.

3. The movement detection and monitoring system of claim 1, wherein the alert message is sent to a healthcare diagnostic device coupled to the server, when the healthcare diagnostic device is in scanning process.

4. The movement detection and monitoring system of claim 3 wherein the server further couples to a door security circuit, wherein if the door security circuit is triggered while the healthcare diagnostic device is in the middle of the scanning process, this server sends a message to the healthcare diagnostic device to pause the scanning process.

5. The movement detection and monitoring system of claim 3 wherein the at least one camera comprises at least two cameras, wherein if the server detects a movement above the threshold from the output image signals of any one of the at least two cameras, the server outputs the alert message to pause the scan.

* * * * *